US011675197B1

(12) United States Patent
Fernandez

(10) Patent No.: US 11,675,197 B1
(45) Date of Patent: Jun. 13, 2023

(54) SYSTEM AND METHOD FOR AUTOMATIC VISION CORRECTION IN NEAR-TO-EYE DISPLAYS

(71) Applicant: United Services Automobile Association (USAA), San Antontio, TX (US)

(72) Inventor: Amanda D. Fernandez, San Antonio, TX (US)

(73) Assignee: United Services Automobile Association (USAA), San Antonio, TX (US)

(*) Notice: Subject to any disclaimer, the term of this patent is extended or adjusted under 35 U.S.C. 154(b) by 0 days.

(21) Appl. No.: 17/661,694

(22) Filed: May 2, 2022

Related U.S. Application Data

(60) Continuation of application No. 17/108,766, filed on Dec. 1, 2020, now Pat. No. 11,360,313, which is a (Continued)

(51) Int. Cl.
 *G02B 27/01* (2006.01)
 *A61B 3/103* (2006.01)
 (Continued)

(52) U.S. Cl.
 CPC .......... *G02B 27/0172* (2013.01); *A61B 3/103* (2013.01); *G02B 26/0825* (2013.01); (Continued)

(58) Field of Classification Search
 CPC ............ G02B 27/0172; G02B 26/0825; G02B 26/0833; G02B 2027/011; H04N 13/344; A61B 3/103; G06T 5/006
 See application file for complete search history.

(56) References Cited

U.S. PATENT DOCUMENTS 4,514,048 A  4/1985  Rogers
6,081,388 A  6/2000  Widl
(Continued)

OTHER PUBLICATIONS

Gregory Kramida, "Resolving the Vergence-Accommodation Conflict in Head-Mounted Displays", <https://www.cs.umd.edu/sites/default/files/scholarly_papers/Kramidarev.pdf>, IEEE Transactions on Visualization and Computer Graphics (V: 22, Issue: 7); Jul. 1, 2016; 17 pages.

(Continued)

*Primary Examiner* — Stephen G Sherman
(74) *Attorney, Agent, or Firm* — BakerHostetler

(57) ABSTRACT

Systems and methods for auto-calibrating a virtual reality (VR) or augmented reality (AR) head-mounted display to a given user with a refractive condition without adding corrective lenses to optical elements of the head-mounted display and without requiring subjective refraction procedures. A method comprises projecting a grid onto an eye of a user using a light source of a head-mounted display worn by the user, capturing the grid as-reflected from the eye using a camera of the head-mounted display, determining a pattern of a reflection of the grid based on the grid as-reflected, generating an aberration map based on a difference between the pattern as-reflected and the grid as-projected, and determining a correction to apply to at least one viewing lens of the head-mounted display worn by the user based on the aberration map.

20 Claims, 5 Drawing Sheets

Related U.S. Application Data division of application No. 16/143,158, filed on Sep. 26, 2018, now Pat. No. 10,890,767.

(60) Provisional application No. 62/564,094, filed on Sep. 27, 2017.

(51) Int. Cl.
*G06T 5/00* (2006.01)
*H04N 13/344* (2018.01)
*G02B 26/08* (2006.01)

(52) U.S. Cl.
CPC .......... *G02B 26/0833* (2013.01); *G06T 5/006* (2013.01); *H04N 13/344* (2018.05); *G02B 2027/011* (2013.01)

(56) References Cited

U.S. PATENT DOCUMENTS

| | | | |
|---|---|---|---|
| 6,256,094 | B1 | 7/2001 | Eyolfson et al. |
| 6,369,954 | B1 | 4/2002 | Berge et al. |
| 6,437,925 | B1 | 8/2002 | Nishioka |
| 6,747,806 | B2 | 6/2004 | Gelbart |
| 7,099,063 | B2 | 8/2006 | Greywall |
| 8,730,129 | B2 | 5/2014 | Solomon |
| 2006/0028400 | A1 | 2/2006 | Lapstun et al. |
| 2009/0015787 | A1* | 1/2009 | Guillen ................ A61B 3/1015 351/205 |
| 2009/0295683 | A1 | 12/2009 | Pugh et al. |
| 2010/0123873 | A1 | 5/2010 | Raymond et al. |
| 2014/0168783 | A1 | 6/2014 | Luebke et al. |
| 2014/0340390 | A1 | 11/2014 | Lanman et al. |
| 2016/0066780 | A1 | 3/2016 | Pamplona et al. |
| 2016/0091720 | A1 | 3/2016 | Stafford et al. |
| 2016/0110920 | A1 | 4/2016 | Schowengerdt |
| 2016/0157716 | A1 | 6/2016 | Pamplona et al. |
| 2016/0205298 | A1 | 7/2016 | Zhou |
| 2016/0270656 | A1 | 9/2016 | Samec et al. |
| 2016/0314564 | A1 | 10/2016 | Jones et al. |
| 2017/0000329 | A1 | 1/2017 | Samec et al. |
| 2017/0325682 | A1 | 11/2017 | Liang |

OTHER PUBLICATIONS

Jennifer Kite-Powell, "EyeNetra Wants to Create Prescription Virtual Reality Screens", https://www.forbes.com/sites/jenniferhicks/2015/10/19/eyenetra-wants-to-create-prescription-virtual-reality-screens/#b6631d95f286 <https://www.forbes.com/sites/jenniferhicks/2015/1 0/19/eyenetra-wants-to-create-prescription-virtual-reality-screens/> Forbes, Oct. 19, 2015.

Scott M. Jobling, "Adaptive Optics for Improved Mode-Coupling Efficiencies", <https://experts.illinois.edu/en/publications/adaptive-optics-for-improved-mode-coupling-efficiencies-2>, Thesis for Master of Science in Electrical and Computer Engineering in the Graduate College of the University of Illinois at Urbana-Champaign; Oct. 19, 2008; 101 pages.

Netra Inc. Cambridge MA, "Netra v1 .01 User Manual", <https://eyenetra.com/manual/netra.pdf>; Nov. 8, 2017; 2 pages.

Vitor Fernando Pampona, "Interactive Measurements and Tailored Displays for Optical Aberrations of the Human Eye", Thesis for the degree of Doctor of Computer Science—Universidade Federal Do Rio Grande Do Sul Instituto De Informatica; Jul. 2012; 159 pages.

Daniel Pohl, et al., "Using Astigmatism in Wide Angle HMDs to Improve Rendering", IEEE virtual reality conference 2015, Mar. 23, 2015; 2 pages.

Jason Orlosky et al., "ModulAR: Eye-Controlled Vision Augmentations for Head-Mounted Displays", IEE Transactions on Visualization and Computer Science; Jul. 2015; 10 pages.

Steve Grogorick et al.; "An Affordable Solution for Binocular Tracking and Calibration in Head-mounted Displays", Proceedings of the 23rd ACM international conference on Multimedia, pp. 15-24; Oct. 2015; 10 pages.

Sheng Liu et al., "An Optical See-Through Head Mounted Display with Addressable Focal Planes", IEEE International Symposium on Mixed and Augmented Reality 2008; Sep. 15, 2008; 10 pages.

Wolfgang Wesemann; "Accuracy and accommodation capability of a handheld autorefractor", J. Cataract Refract. Surg. vol. 26 pp. 62-70; Jan. 2000; 9 pages.

George-Alex Kouleris, "Accommodation and Comfort in Head-Mounted Displays", ACM Transactions on Graphics, Association for Computing Machinery 2017, 36(4}; May 29, 2017; 11 pages.

* cited by examiner

SYSTEM AND METHOD FOR AUTOMATIC VISION CORRECTION IN NEAR-TO-EYE DISPLAYS

CROSS-REFERENCE TO RELATED APPLICATION

The present application claims benefit of and is a continuation application which application claims benefit of U.S. patent application Ser. No. 17/108,766, filed Dec. 1, 2020, which application is a divisional of and claims benefit of U.S. patent application Ser. No. 16/143,158 (U.S. Pat. No. 10,890,767), filed Sep. 26, 2018 (Issued Jan. 12, 2021), which application claims benefit of and priority to U.S. Provisional App. No. 62/564,094, filed Sep. 27, 2017, which is incorporated by reference in its entirety.

TECHNICAL FIELD

The present disclosure relates generally to virtual reality and augmented reality head-mounted displays, and more particularly to systems and methods for automatic vision correction in near-to-eye head-mounted displays.

BACKGROUND

Virtual reality and augmented reality head-mounted displays are devices worn on or mounted to the user's head that create a near-to-eye display. A virtual reality display, or "VR" display, typically presents digital or virtual image information without transparency to real-world visual input. An augmented reality display, or "AR" display, typically presents digital or virtual image information as an augmentation to visualizing the real physical environment around the user.

Generally, VR and AR head-mounted displays are designed to synthesize light fields corresponding to virtual objects within a viewer's natural accommodation range. VR and AR head-mounted displays employ a number of optical elements including the displays, intermediate optical elements (lenses, mirrors, prisms, etc.), and the user's pupils. Setting up a VR or AR headset for a given user can be time-consuming, and can be especially challenging for users that have refractive aberrations. One approach is for the user who has a refractive aberration to select and manually attach user-selected corrective lenses, such as prescription refractive lenses, during set-up of a VR or AR head-mounted display. However, it would be highly desirable to avoid the need for this manual procedure when setting up a VR or AR head-mounted display for a user with a refractive condition.

There is a need for a system and method for calibrating VR and AR head-mounted displays for users with refractive aberrations that avoid the need for selecting and attaching corrective lenses. Additionally, there is a need for a method for calibrating VR and AR head-mounted displays that avoids the need to add user-customized corrective lenses, such as prescription refractive lenses, to the optical elements of the head-mounted display. There is also a need for a method for automatically calibrating VR and AR head-mounted displays that avoids the need for subjective refraction procedures. There is also a need for a method for calibrating VR and AR head-mounted displays that facilitates use of a given head-mounted display by both normal-vision users and defective-vision users, without requiring time-consuming manual recalibration when switching between users.

SUMMARY

Embodiments described herein include virtual reality (VR) and augmented reality (AR) head-mounted displays capable of presenting near-to-eye images with accommodation, convergence, and binocular disparity that are corrected for the refractive aberration of a given user. A refraction headset associated with the VR or AR head-mounted display automatically collects objective refraction data for a user of the head-mounted display representative of a refractive aberration of at least one of the eyes of the user. The refraction headset communicates the objective refraction data to the VR or AR head-mounted display, which processes this data to auto-calibrate images displayed by the device to the given user to compensate for a refractive aberration in one or both eyes of the user. The present methods and systems do not require collecting subjective refraction information from the user, and do not require the step of adding user-customized corrective eyewear to optical elements of the near-to-eye head-mounted display to compensate for the user's refractive aberration.

In an embodiment, a method comprises projecting a grid onto an eye of a user using a light source of a head-mounted display worn by the user; capturing the grid as-reflected from the eye using a camera of the head-mounted display; determining a pattern of a reflection of the grid based on the grid as-reflected; generating an aberration map based on a difference between the pattern as-reflected and the grid as-projected; and determining a correction to apply to at least one viewing lens of the head-mounted display worn by the user based on the aberration map.

In another embodiment, a system comprises a head-mounted display configured to display images corresponding to virtual reality or augmented reality; a light source of the head-mounted display configured to project a grid onto an eye of a user; and a camera of the head-mounted display configured to capture the grid as-reflected from the eye of the user. The system also comprises a server communicatively coupled to the head-mounted display and configured to: determine a pattern of a reflection of the grid based on the grid as-reflected; generate an aberration map based on a difference between the pattern as-reflected and the grid as-projected; and determine a correction to apply to at least one viewing lens of the head-mounted display worn by the user based on the aberration map.

In another embodiment, a computer program product comprising a non-transitory computer-readable medium storing instructions that when used effectuate: projecting a grid onto an eye of a user using a light source of a head-mounted display worn by the user; capturing the grid as-reflected from the eye using a camera of the head-mounted display; determining a pattern of a reflection of the grid based on the grid as-reflected; generating an aberration map based on a difference between the pattern as-reflected and the grid as-projected; and determining a correction to apply to at least one viewing lens of the head-mounted display worn by the user based on the aberration map.

Other objects, features, and advantages of the present disclosure will become apparent with reference to the drawings and detailed description of the illustrative embodiments that follow.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

DETAILED DESCRIPTION

Figure 1:
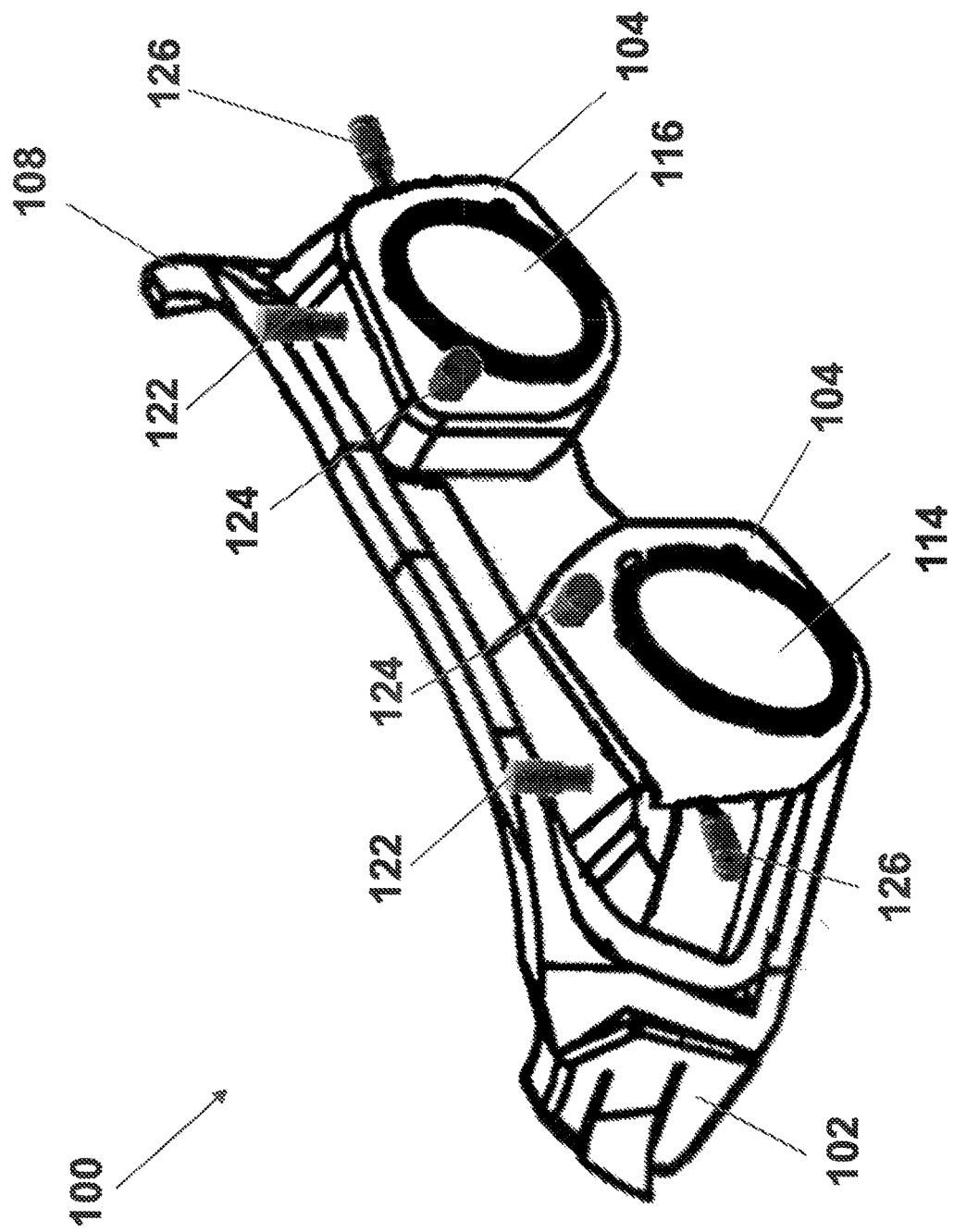
FIG. 1 is a perspective view of stand-alone automated refraction headset, in accordance with an embodiment.

In the following detailed description, reference is made to the accompanying drawings, which depict non-limiting, illustrative embodiments of the present disclosure. Other embodiments may be utilized and logical variations, e.g., structural and/or mechanical, may be implemented without departing from the scope of the present disclosure. To avoid unnecessary detail, certain information, items, or details known to those skilled in the art may be omitted from the following.

In virtual reality (VR) and augmented reality (AR) systems, a user primarily interacts with the virtual environment through a near-to-eye display. In conventional near-to-eye displays for VR and AR systems, in front of each eye a small physical display is placed behind a magnifying lens, creating a virtual image at some fixed distance from the viewer. Small differences in the images displayed to the two eyes can create a vivid perception of depth, or stereopsis. In virtual reality (VR) and augmented reality (AR) systems in the form of head-mounted displays, as in the present disclosure, the display system is a near-to-eye display device mounted to or worn at the user's forehead, such as a harness or helmet. As used in the present disclosure, the term "near-to-eye display" means a virtual reality head-mounted display or an augmented reality head-mounted display.

A substantial portion of potential users of VR and AR systems have visual impairments such as refractive errors. Refractive errors such as myopia and hyperopia are extremely common visual impairments in which the eye's lens does not produce a sharp image on the retina for objects at particular distances. Although these impairments can often be corrected with contact lenses or surgery, many people wear eyeglasses. In various current virtual reality and augmented reality head-mounted displays, users are required to wear their glasses beneath the display system, which in other head-mounted displays do not permit users to wear their glasses. Although wearing glasses is technically possible with some systems, users often experience problems with fit and comfort. These problems are likely to increase as the form factor of near-to-eye displays decreases. The systems and methods of the present disclosure address these problems.

The present disclosure describes systems and methods for determining refractive aberrations for a given user of a virtual reality head-mounted display or an augmented reality head-mounted display ("HMD"), and for automatically calibrating the head-mounted display to compensate for the determined refractive aberrations (also herein called auto-calibration of the head-mounted display). Auto-calibration of the head-mounted display presents adjusted virtual images to the user, these images being corrected in accordance with the user's refractive condition. In various embodiments, the corrected images substantially increase the perceived sharpness of targets at varying distances as viewed by users with refractive conditions, e.g., via selected magnification of stereoscopic images. Additionally, in various embodiments, the corrected images increase the ability of impaired-vision users to fuse targets, i.e., to avoid diplopia or double vision.

The systems and methods of the present disclosure do not require the user to add user-customized corrective eyewear to the near-to-eye head-mounted display. As used in the present disclosure, adding user-customized corrective eyewear means that the user wears or otherwise manually adds eyeglasses or other corrective lenses to the optical elements included in the head-mounted display, thereby to correct for the refractive aberration of the user in images viewed by the user.

Additionally, the present methods for setting up a near-to-eye head-mounted display do not require users to carry out subjective retraction procedures.

Virtual reality head-mounted displays (also herein called VR headsets) include a stereoscopic display, a display device that provides separate images for each eye. VR head-mounted displays may incorporate integrated displays, or may be designed to enclose a separate mobile personal computer device, such as a smartphone. In the latter case, the enclosed display device provides the stereoscopic display. In either type of VR head-mounted display, light propagated by the stereoscopic display is transmitted through optical elements of the head-mounted display, such as lenses, in a path extending optically between the display device and the user's eyes, herein referred to as the "optical path" of the head-mounted display. VR head-mounted displays may include other features such as stereo sound and head motion tracking sensors. Head motion tracking sensors in VR head-mounted displays can include gyroscopes, accelerometers, and structured light systems, among others.

Augmented reality head-mounted displays (also herein called AR headsets) provide a live direct or indirect view of the user's physical, real-world environment. These real-world elements are "augmented" by computer-generated imagery (CGI), such as video and graphics. The AR head-mounted display is a near-to-eye display device mounted to or worn at the user's forehead, such as a harness or helmet that places images of the physical world and virtual objects over the user's field of view.

One type of AR display, sometimes called an "optical see-through" display, combines the real-world view with CGI by projecting the CGI through a partially reflective mirror onto viewing lens(es), viewing the real world environment directly through the lens(es). In this type of AR headset, light projected by an optical projector is propagated through optical elements of the head-mounted displays, such as lenses, in an optical path of the head-mounted display between the projector and the user's eyes.

Another type of AR display, sometimes called a "video see-through" display, combines the real-world view with CGI electronically. Typically this is done by receiving video images of the real-world environment from a camera, and mixing the video electronically with CGI, e.g., using an optical combiner. In this type of AR headset, the optical path includes the optical combiner and all other optical elements in the paths between the sources of both the video images and CGI, and the user's eyes.

An AR head-mounted display may overlay information about the environment and its objects onto the real world elements of the display. This information can be virtual or real, e.g., can show sensed or measured data overlaid in exact alignment with locations of the sensed or measured physical objects in space. AR head-mounted displays may include other media such as stereo sound, and other features such as head motion tracking sensors. Head motion tracking sensors can include gyroscopes, accelerometers, and structured light systems, among others.

VR and AR head-mounted displays may be transparent or opaque, depending on the application. For example, a transparent AR head-mounted display can overlay information and graphics on top on the real world, while an opaque VR or AR head-mounted display can provide an immersive theater-like experience. Immersive head-mounted displays block a user's view of the real world and create a large field of view image, e.g., a 90°+ degrees field of view for VR head-mounted displays. In various embodiments, optical see-through AR head-mounted displays leave the user's view of the real world open and create either a transparent image or a small opaque image that blocks only a small portion of the user's field of view. In an illustrative augmented reality headset, the headset provides a direct view of the physical environment through lenses within a field of view (e.g., within a given range of angles such as 20°-60°), and overlays CGI on top of the user's direct view of the real world.

In various embodiments, the VR or AR head-mounted display incorporates an automated refraction headset, also herein sometimes called simply a refraction headset, to automatically collect refractive aberration measurements for the user. The automated refraction headset communicates refractive condition data based on these measurements to the VR or AR head-mounted display, for auto-calibration of the head-mounted display. In an embodiment, the automated refraction headset is permanently or temporarily integrated into the head-mounted display, and the user wears the head-mounted display during measurement of the user's refractive aberration. In another embodiment, the automated refraction headset is separate from the VR or AR head-mounted display, and communicates the refractive condition data to the head-mounted display.

As used in the present disclosure, an automated refraction headset is a binocular headset that is either a separate device from the VR or AR headset (also herein called a stand-alone device), or that is permanently or temporarily integrated into the head-mounted display. The automated refraction headset automatically collects objective measurements of refractive aberration for the user. During collection of objective measurements of refractive aberration, the user is not required to provide subjective inputs, such as subjective information on viewed images, or selection of corrective lenses. In various embodiments, the automated refraction headset incorporates an autorefractor, or a wavefront aberrometer, to collect objective measurements of refractive aberration for the user. In some embodiments, in addition to providing objective measurements of refractive aberration of the user, the automated refraction headset provides other objective ophthalmic measurements of the user.

In an embodiment, the automated refraction headset incorporates an infrared autorefractor. Infrared autorefractors provide an objective and precise measurement of the accommodation response. In an embodiment, the infrared autorefractor includes an infrared source, a fixation target and a Badal optometer. The infrared autorefractor detects the reflections from a cone of infrared light. These reflections are analyzed to determine the size and shape of the ocular fundus at the back of the eye. By measuring this zone, the infrared autorefractor determines when a user's eye properly focuses on an image. The autorefractor automatically changes the magnification of the observed image until the image comes into focus. In an embodiment, the infrared autorefractor repeats this process in at least three meridians of the eye, and the autorefractor calculates the refraction of the eye, sphere, cylinder and axis. The autorefractor then monitors the magnification setting and determines the level of refractive correction needed. In the present disclosure, these calculations of refractive correction are called refractive condition data. In an embodiment, for refractive aberrations involving cylindrical error, the refractive condition data provided by the autorefractor includes the axis of the cylindrical error.

In another embodiment, the automated refraction headset incorporates a wavefront aberrometer. The wavefront aberrometer projects a wavefront of light through the refractive components of the eye (cornea and crystalline lens), and measures distortions that occur as light travels through the eye, i.e., refractive aberrations. In an illustrative wavefront aberrometry procedure, in a first step the wavefront aberrometer measures pupil diameter, and uses this measurement to derive a reference wavefront shape representing a theoretically perfect eye. The aberrometer then projects a beam of light into the user's eye, and the wavefront of light reflected by the retina is captured by the aberrometer. The aberrometer then creates a wavefront map of the eye by comparing the shape of the captured wavefront with a pre-programmed reference wavefront, measuring all points of difference between the two. For example, a wavefront map in the form of a flat, circular plane represents a theoretically perfect (emmetropic) eye that exactly matches the diameter of the pupil. In the present disclosure, the wavefront map generated by a wavefront aberrometer is sometimes called an aberration map.

In some embodiments, the VR or AR head-mounted display is designed for use with an enclosed mobile personal computer device, such as a smartphone, to provide a stereoscopic display. In an embodiment, the automated refraction headset is configured for use with the mobile computing device. In an embodiment, a camera of the mobile computing device captures images generated by the automated refraction headset.

FIG. 1 illustrates the exterior design of a stand-alone automated refraction headset 100 according to the present disclosure, i.e., a refraction headset that is separate from a VR or AR head-mounted display. The automated refraction headset 100 is a goggle-based system including a goggle frame or base 102 configured to fit onto the user's head. The base 102 supports left and right ocular assemblies 104, 106, which house components of a binocular objective autorefractor system (not shown). Automated refraction headset 100 provides a wearable, mobile device for automatic objective refraction measurements. Automated refraction headset 100 enables objective refraction measurements of the user in a free posture. Refraction headset 100 may be worn by the user during collection of objective refraction measurements of the user, then the user can conveniently remove the refraction headset and put on a separate VR or AR head-mounted display (not shown). The separate VR or AR head-mounted display is automatically calibrated to correct for the user's refractive aberration based on the objective refraction measurements, and during auto-calibration the automated refraction headset is in wired or wireless electrical communication with the head-mounted display.

In an embodiment, automated refraction headset 100 constitutes an occluded binocular autorefraction device, including front-mounted occluded eyepieces 112, 116 respectively mounted to the front of left and right ocular assemblies 104, 106. Left and right ocular assemblies 104, 106 contain various working components of an autorefractor device, such as a light source that projects a light pattern, e.g., in the shape of a ring or other form, to the retina at the back of the user's respective eye. Other working components include a camera or other sensor in each ocular assembly to measure the reflected image, and optical elements such as lenses in the paths of projected and reflected light patterns. In an embodiment, for each eye of the user, the refraction headset 100 automatically changes magnification settings until the reflected image comes into focus. Compact arrangements of light sources, sensors, and other electro-optical components suitable for the binocular autorefraction headset 100 are known in the art.

In an embodiment, the base 102 of refraction headset 100 includes a skirt 108 that conforms to the user's face and that distributes forces around the face. The headset 100 may include a harness, straps, or other mechanism (not shown) for fastening the headset over and around the user's head. The refraction headset be adjusted to fit a variety of users with different shaped heads. In an embodiment, automated refraction headset 100 incorporates mechanisms to reposition components of the eye assemblies including controls 122 for adjusting bridge height, controls 124 for adjusting vertex distance, and controls 126 for adjusting interpupillary distance (IPD).

In various embodiments, automated refraction headset 100 is configured to communicate objective refraction measurements, such as sphere, cylinder, and axis measurements, to a VR or AR head-mounted display (not shown) via wired or wireless communications. These objective refraction measurements are processed by the head-mounted display for auto-calibration of displayed images to compensate for the user's refractive aberrations. In an embodiment, in addition to automated objective refraction measurements, refraction headset 100 may automatically perform other objective ophthalmic measurements besides objective refraction measurements. Results of these additional ophthalmic measurements can be communicated to a VR or AR head-mounted display and used to auto-calibrate the head-mounted display to correct for other visual impairments.

Figure 2:
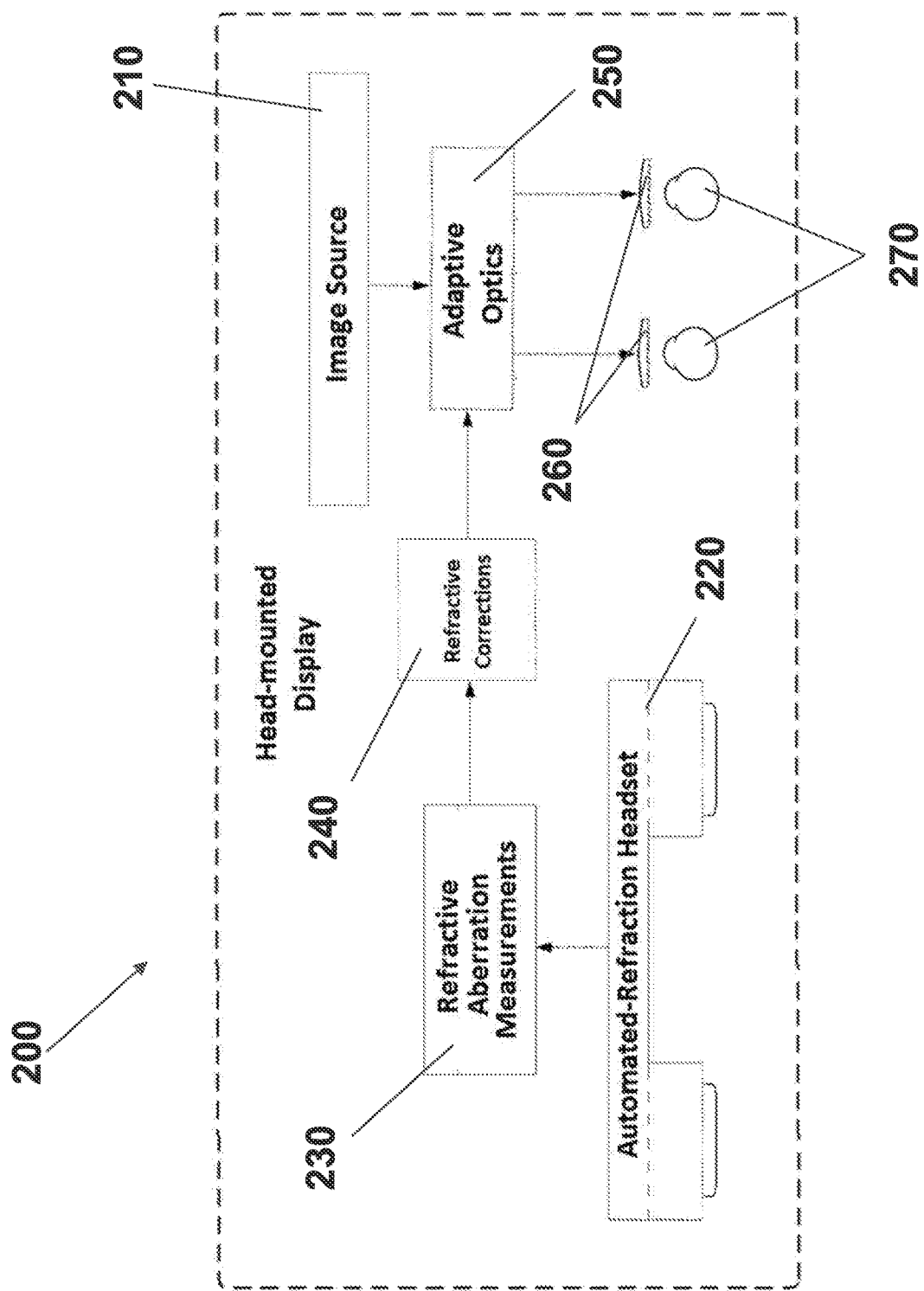
FIG. 2 is a schematic diagram of a near-to-eye head-mounted display with an automatic refraction headset sub-assembly, in accordance with an embodiment.
Figure 3:
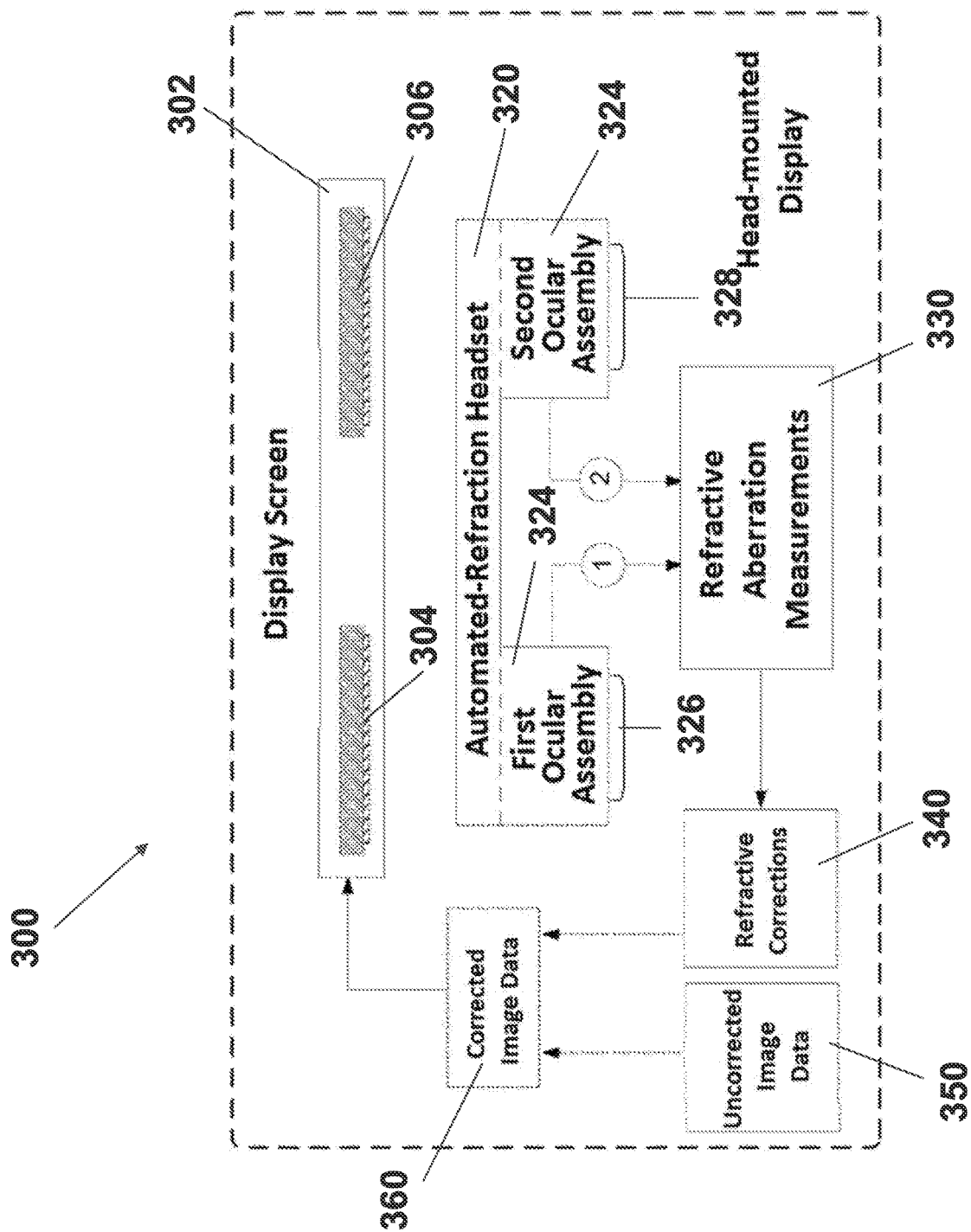
FIG. 3 is a schematic diagram of a near-to-eye head-mounted display with an automatic refraction headset sub-assembly, in accordance with an embodiment.

In the embodiments of FIGS. 2 and 3, the automated refraction headset comprises a temporary or permanent subassembly of a VR or AR head-mounted display. The refraction headset subassembly may be positioned in-line with the optics path of the head-mounted display, such as shown at 320 in FIG. 3, or may be positioned in an alternative location, such as shown at 220 in FIG. 2. In some embodiments, the refraction headset subassembly is displaced and/or pivoted within the VR or AR head-mounted display for access by the user in collecting objective refraction measurements. Where refraction headset subassembly is positioned in-line with the optics path of the head-mounted display, one or more optical elements of the head-mounted display may be temporarily repositioned to make room for the refraction headset subassembly.

In an embodiment, the automated refraction headset subassembly incorporates certain optical components that are also used in the head-mounted display, such as a left viewing lens 326 for the user's left eye and a right viewing lens 328 for the user's right eye (FIG. 3). In another example, the automated refraction headset incorporates mechanisms for adjusting the automated refraction headset to fit the user's facial configuration (e.g., via adjustments to bridge height, vertex distance, or interpupillary distance), which mechanisms are also used in the head-mounted display.

In various embodiments, the automated refraction headset provides refractive condition data, these refractive condition data indicating refractive aberrations for one or both eyes of the user. In the present disclosure, refractive aberrations are also referred to refractive conditions, or refractive errors. In various embodiments, the refractive aberration includes spherical errors, wherein the optical power of one or both eye is either too large or too small to focus light on the retina. In various embodiments, the refractive aberration includes cylindrical errors, wherein the optical power of the eye is too powerful or too weak across one meridian.

In various embodiments, the refractive condition includes myopia, also called nearsightedness. In an embodiment, the myopia is refractive myopia, arising from a cornea or crystalline lens with too much curvature. In an embodiment, the myopia is axial myopia, arising from an eyeball that is too long. In various embodiment, the refractive condition includes hyperopia, also called farsightedness. In an embodiment, the hyperopia is refractive hyperopia, arising from a cornea or crystalline lens with insufficient curvature. In an embodiment, the hyperopia is axial hyperopia, arising from an eyeball that is too short. In an embodiment, the refractive condition includes presbyopia. In an illustrative embodiment, symptoms of presbyopia include difficulties in near vision.

In various embodiments, the refractive aberration indicated by the refractive condition data includes cylindrical errors. In various embodiments, refractive condition data for cylindrical errors includes the axis of the cylindrical error, i.e., the angle between the meridian and the horizontal. In an embodiment, the cylindrical error is caused by a corneal curvature tending towards a cylindrical shape. In various embodiments, the refractive condition includes astigmatism. In typical symptoms of astigmatism, the user sees lines of a particular orientation less clearly than lines at right angles to this orientation. In another embodiment, the refractive condition includes mixed astigmatism. In typical symptoms of mixed astigmatism, the user's vision is myopic in a given direction, and hyperopic at right angles to the direction of myopia.

The refraction headset can identify various binocular vision anomalies, such as tropias or conditions in which the eyes do not properly align with each other when looking at an object, and suppression of an eye, i.e. subconscious adaptations by a person's brain to eliminate the symptoms of disorders of binocular vision. Binocular vision anomalies can result in various disparities of vision between left eye and right eye, and between different fields of view of one or both eyes, such as upper and lower fields as in bifocal optics. The present systems and methods can adapt to these binocular vision anomalies, e.g., by making different image adjustments respectively to left and right stereoscopic images. In an illustrative embodiment, due to an extreme binocular vision disorder one eye has little or no vision, and the user depends completely or nearly completely on vision of the other eye. In this example, the methods and systems of the present disclosure can adjust stereoscopic images designed for normal-vision users to provide monoscopic imagery that relies upon the images for the user's "good" eye.

In additional embodiments, the refractive condition includes higher-order aberrations in the eye, such as coma, spherical aberration or keratoconus.

Figure 4:
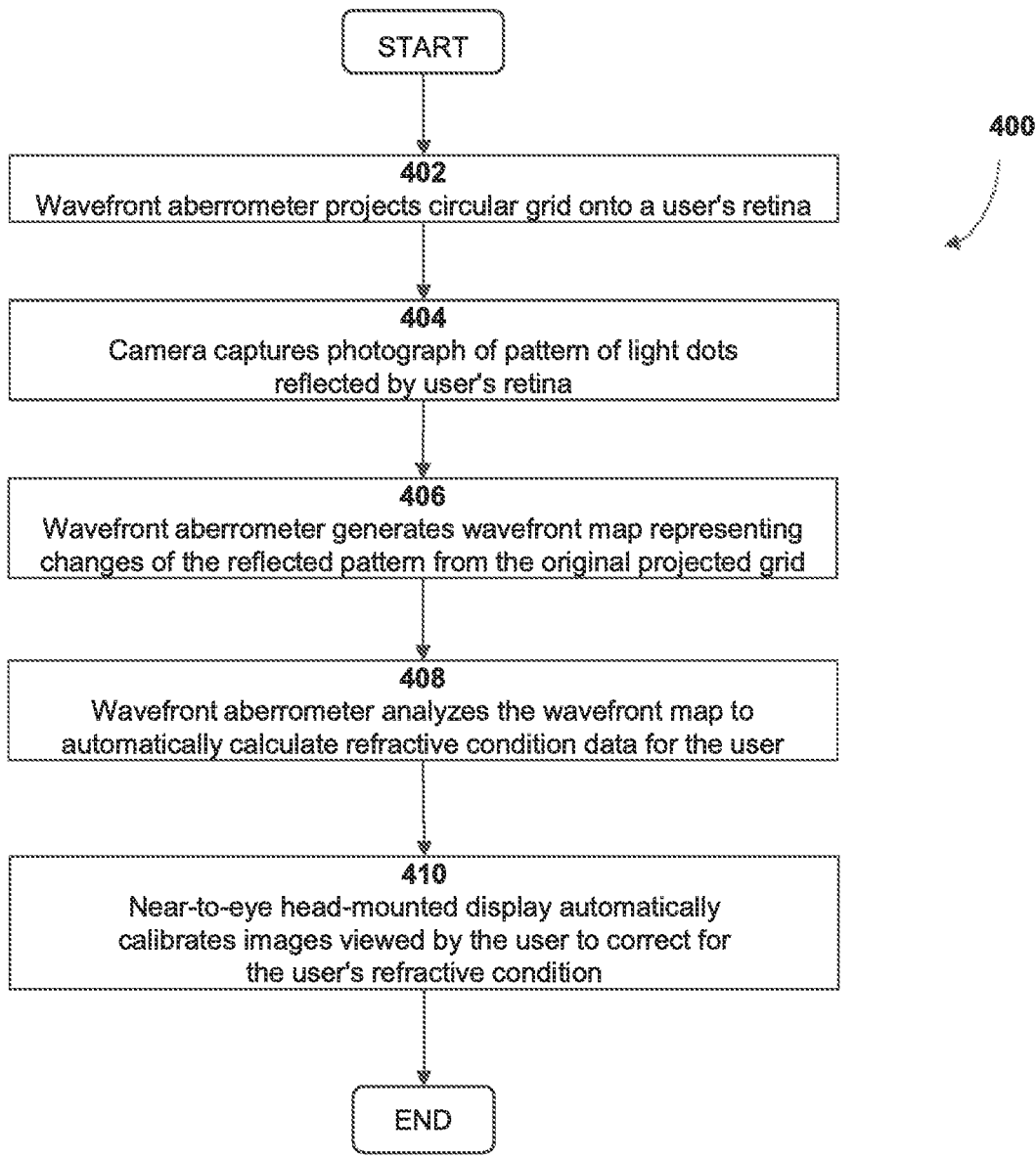
FIG. 4 illustrates a method for automated correction of images viewed by a user of a near-to-eye display, based on objective refraction measurements for the user collected using wavefront aberrometry, in accordance with an embodiment.

FIG. 4 shows an illustrative method 400 for controlling an AR or VR head-mounted display by diagnosing a refractive condition of a user via an automated refraction headset, then automatically modifying images viewed by the user based on the diagnosed refractive condition. In the method 400, the automated refraction headset of the head-mounted display embodies aberrometry technology. At step 402, the wavefront aberrometer projects a substantially circular grid of light dots onto the user's retina. At step 404, a camera associated with the automated refraction headset takes photographs of a pattern of light dots reflected by the user's retina. In an embodiment, the camera is included in a mobile computing device associated with the AR or VR head-mounted display. At step 406, the wavefront aberrometer generates a wavefront map, also called an aberration map, representing the change of pattern of the light dots reflected by the user's retina from the original pattern of the substantially circular grid of light dots projected onto the user's retina. In an embodiment of step 406, the wavefront aberrometer includes wavefront aberrometry software, which measures the change of the reflected pattern from the original pattern. In an embodiment, the wavefront aberrometry software is stored in a mobile computing device associated with the AR or VR head-mounted display.

At step 408, the wavefront aberrometer analyzes the aberration map to automatically determine refractive condition data for one or both eyes of the user. In an embodiment, a spreading outward of the pattern of reflected dots from the pattern of the original grid indicates that the user has hyperopia. In an embodiment, a convergence of the pattern of reflected dots from the pattern of the original grid indicates that the user has myopia. In an embodiment, a change of the circular pattern of the original grid to an oval pattern of the reflected grid indicates that the user has astigmatism.

At step 410, the imaging system of the AR or VR head-mounted display automatically calibrates images viewed by the user to correct for the refractive aberration indicated by the refractive condition data. In an embodiment of step 410, this step is carried out by an imaging system of the head-mounted display. In an embodiment, step 410 includes modifying images viewed by the user via adaptive optics of the AR or VR head-mounted display. In an embodiment, step 410 includes modifying images viewed by the user by adjusting adaptive optics of the AR or VR head-mounted display. In an embodiment, step 410 includes modifying images viewed by the user via imaging software configured to automatically generate customized displays corrected for the diagnosed refractive aberration of the user. In another embodiment, step 410 includes modifying images viewed by the user via a combination of adjustment of adaptive optics and automatic generation of customized displays.

In an embodiment, the virtual reality or augmented reality head-mounted display includes an optical path consisting of a near-to-eye image source, such as a stereoscopic display or an image projector, and optical elements for guiding light from the near-to-eye image source, such as lenses, waveguides, mirrors, optical prisms, optical waveguides, beam splitters, and beam combiners. These optical elements are located optically between the user's eyes and the near-to-eye image source, i.e., along an "optical path" within the AR or VR head-mounted display. In an embodiment, the near-to-eye image source generates image light representative of a desired image, and the head-mounted display transmits the image light from the near-to-eye image source through the optical elements in the optical path toward the eyes of the user. In various embodiments, an optical path may be a single path from the image source toward the viewer's eyes, or may include multiple branches, such as two branches associated with two different image sources in certain types of AR head-mounted display. In an embodiment, the near-to-eye image source and the optical elements or the AR or VR headset are designed to provide a wide field of view while also providing a comfortable distant point of focus, for both normal-vision users and users with a refractive aberration.

In an embodiment, optical elements of the head-mounted display include adaptive optics. For purposes of this disclosure, the term "adaptive optics" refers generally to one or more adaptable optical element in the optical path of an AR or VR head-mounted display that automatically adjust the optical characteristics of wavefronts in the optical path of the head-mounted display under control of the imaging system of the AR or VR head-mounted display. Adaptive optics are existing optical elements of the AR or VR head-mounted display in the optical path from the display to the eye, and do not include corrective eyewear that the user wears or otherwise manually adds to the head-mounted display to provide refractive correction. The imaging system of the head-mounted display is configured, in the event a given user has a refractive aberration, to automatically adjust the adaptive optics to correct the refractive aberration in images viewed by the given user to improve images viewed by the given user. The term adaptive as used herein may appear in phrases such as "adaptive optics," "adaptive optical elements," and in specific types of adaptive optical elements such as "adaptive lenses" or "adaptive mirrors." Adaptive optics may include individual adaptive optical elements, as well as assemblies or systems of adaptive optical elements.

In various embodiments, the adaptive optics includes one or more variable focus optical element. As used in the present disclosure, a variable focus optical element is configured to vary a focus of light displayed or projected by the head-mounted display, and to transmit the light to the user's eye, under control of an imaging system of the VR or AR head-mounted display. In an embodiment, the variable focus optical element is controlled to vary the focus of the light patterns based at least in part on the refractive condition data measured by the automated refraction headset, to improve an accommodation of the user's eye. In various embodiments, the variable focus optical element is configured to achieve variable focus through refractive, diffractive, or reflective techniques.

In some embodiments, conventional VR and AR displays (near-to-eye displays) employ fixed-focus optical elements, in which a magnified virtual image appears at a constant distance. In such conventional near-to-eye displays, a first image with a relatively short stereoscopic distance can appear at the same virtual image distance as a second image with a relatively long stereoscopic distance. The present AR and VR heat-mounted displays employing adaptive optics, on the other hand, can present different images to the two eyes in which objects can be simulated at varying stereoscopic distances to correct for refractive aberration in images viewed by a given user. In an adaptive optics head-mounted near-to-eye display, virtual image distance can be customized for varying stereoscopic distances of the target for comfortable viewing by a user with a given refractive aberration.

In an embodiment, the virtual reality or augmented reality head-mounted display is configured, in the event the automated refraction headset provides refractive condition data identifying myopia for the given user, to automatically adjust the adaptive optics to cause divergence of light rays traveling through the optical path before an image reaches the eyes of the user. In an embodiment, the virtual reality or augmented reality head-mounted display is configured, in the event the automated refraction headset provides refractive condition data identifying hyperopia for the given user, to automatically adjust the adaptive optics to cause convergence of light rays traveling through the optical path before an image reaches the eyes of the user. In an embodiment, the virtual reality or augmented reality head-mounted display is configured, in the event the automated refraction headset provides refractive condition data identifying cylindrical error (astigmatism) in an identified axis for the given user, to automatically adjust the adaptive optics to propagate increased light in one principal meridian of the cylindrical error, and to propagate reduced light at the other principal meridian, before an image reaches the eyes of the user.

Adaptive optical elements can include, for example, adaptive lenses such as fluidic adaptive lenses with an adjustable focal length (U.S. Pat. No. 6,369,954); adaptable lenses incorporating liquid crystal materials (U.S. Pat. No. 6,437, 925); adaptable lenses controlled by application of pressure (U.S. Pat. No. 6,081,388); reconfigurable elastomeric lenses (U.S. Pat. No. 4,514,048); and lenses based on micro-electromechanical systems ("MEMS"; U.S. Pat. No. 6,747, 806). In an embodiment, the adaptive lens is a refractive optical element, such as a liquid crystal lens. In an embodiment, the adaptive lens is a switchable diffractive optical element.

In the head-mounted display 200 of FIG. 2, image light transmitted by an image source 210 is passed through adaptive optics 250 in an optical path from image source 210 toward the user's eyes (pupils 270). In an embodiment, image light received from adaptive optics 250 is viewed by the user at viewing lenses 260. Refraction headset 220 automatically effects objective refraction examination of the user's vision, collecting refractive aberration measurements 230. The refractive aberration measurements 230 are processed by the automated-refraction headset, and/or by a control system of the head-mounted display 200, to calculate refractive corrections 240 for the user's vision. In various embodiments, the head-mounted display 200 controls the adaptive optics 250 based upon the refractive corrections 240 to modify the image light transmitted through the adaptive optics toward the user's pupils 270 to compensate for the refractive aberration of the users in images viewed by the user at viewing lenses 260. In an embodiment, in addition to adaptive optics 250, the optical path also may include fixed-optics elements, which may include the viewing lenses 260. In an embodiment, the adaptive optics 250 include the viewing lenses 260.

In various embodiments of the adaptive-optics head-mounted display of FIG. 2, the image source 210 is a micro-display of a VR head-mounted display, and the adaptive optics 250 includes a variable focus lens assembly. Light received from micro-display 210 is passed through the variable focus lens assembly 250 to viewing lenses 260. Depending upon the controlled focus of the variable focus lens assembly, light entering the pupils 270 will have various levels of focus. A collimated flat wavefront represents optical infinity, while increased beam divergence and wavefront curvature represents closer viewing distance relative to pupils 270. In another embodiment, the image source 210 is a stereoscopic display of a VR head-mounted display that provides image data, and one or more optical element(s) that converge light patterns associated with the image data to a first focus. A variable focus lens assembly 250 modifies the first focus of the light patterns to produce a wavefront at a second focus. In an embodiment, the second focus is a controlled depth of focus that corrects for the user's refractive condition.

Adaptive optical elements also can include adaptive mirrors, which employ reflective surfaces for the implementation of wavefront correction. Two broad classes of adaptive mirrors are segmented mirrors and deformable mirrors. Segmented mirrors incorporate arrays of independently controlled mirrors. For example, segmented mirrors include mirrors based on "MEMS" technology (U.S. Pat. No. 7,099, 063). Deformable mirrors include various types of deformable-membrane mirrors, such as piezoelectric mirrors (U.S. Pat. No. 8,730,129, advanced immersive visual display system). In various embodiments, adaptive mirrors using segmented MEMS technology entail lower manufacturing costs than deformable mirrors, and can employ standard semiconductor fabrication processes such as deposition, etching, lithography and substrate bonding. In an embodiment, the adaptive mirror is an opaque reflective mirror. In another embodiment, the adaptive mirror is a partially reflective mirror.

In various embodiments of the head-mounted display of FIG. 2, the image source 210 is an optical projector of an AR head-mounted display, and the adaptive optics 250 includes a variable focus mirror. In an embodiment, an image source 210 is a DLP ("Digital Light Processing") projector of an AR head-mounted display 200. DLP projector 210 projects CGI images at a given frame rate, and AR head-mounted display 200 selectively passes the projected light onto viewing lenses 260 via an adaptive mirror assembly 250. DLP projectors employ an optical micro-electro-mechanical technology that uses a digital micro-mirror device, originally developed by Texas Instruments Incorporated, Dallas Tex. In an embodiment, adaptive mirror assembly 250 is a high-frequency variable focus mirror, such as a deformable membrane mirror, which selectively passes the projected CGI onto the viewing lenses 260 at the same frame rate as the frame rate of DLP projector 210. The high-frequency variable focus mirror changes the focus of CGI images viewed by the user through the viewing lenses 260 on a frame-by-frame basis to correct for the user's refractive condition, based on refractive aberration measurements 230 received from automated refraction headset 220.

Figure 5:
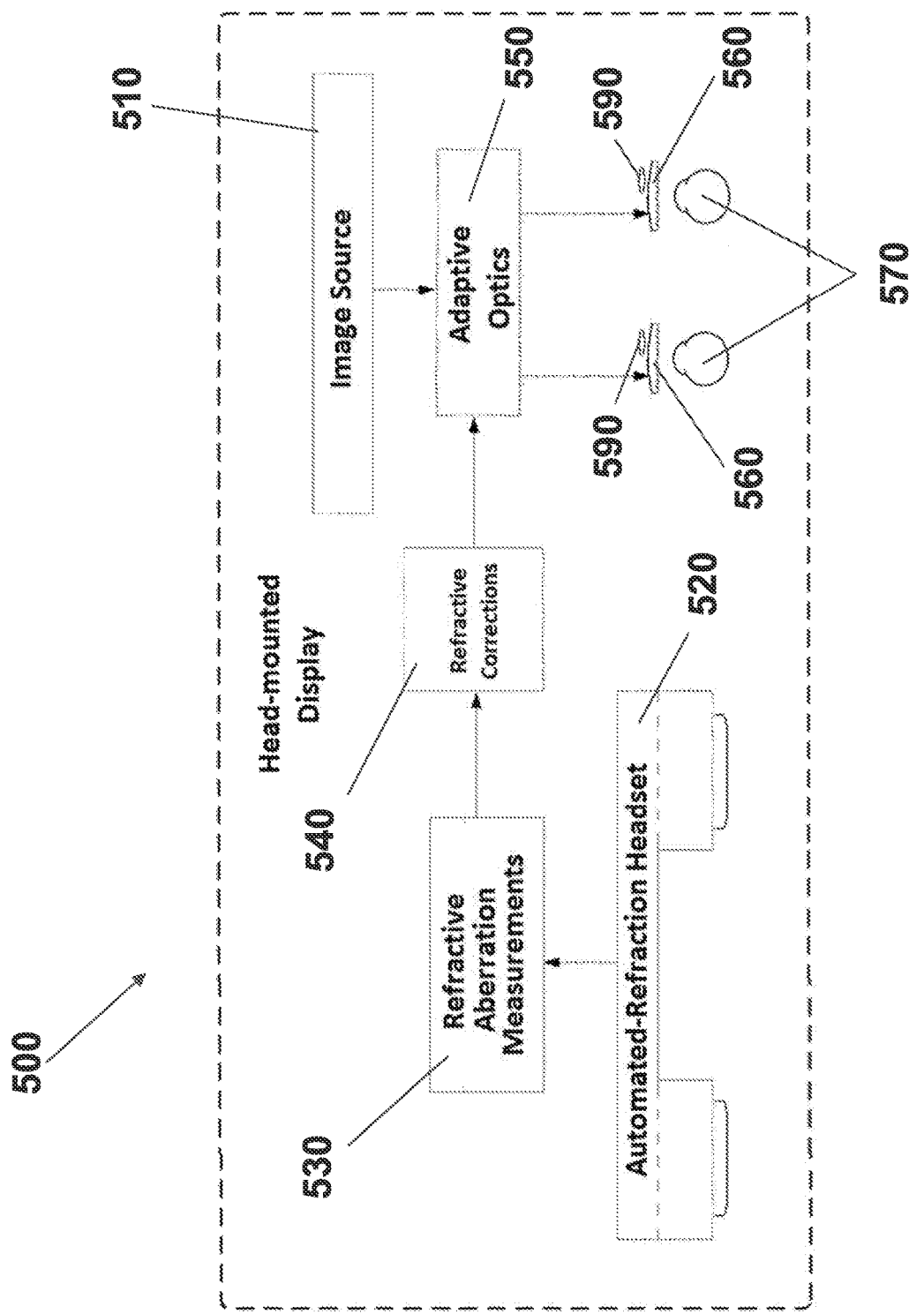
FIG. 5 is a schematic diagram of a near-to-eye head-mounted display with an automatic refraction headset sub-assembly, in accordance with an embodiment.

The head-mounted near-eye display 500 of FIG. 5 has components that generally correspond to the head-mounted display 200 of FIG. 2, except for elements 560, 590. Optical elements 560, 590 are lenses for viewing images in an optical see-through type AR head-mounted display 500. Viewing lenses 560 provide a direct view of the user's physical environment, overlaid with computer-generated imagery received from an optical projector 510 via adaptive optics 550. AR display 500 includes adaptive lenses 590, which act as a secondary lens in conjunction with viewing lenses 560 to automatically correct for the user's refractive aberration in the user's view of the physical environment through viewing lenses 560.

In an embodiment, the virtual reality or augmented reality head-mounted display includes imaging software configured to control imaging into the eyes of the user, to determine the user's view of virtual reality (VR) or augmented reality (AR) images. In an embodiment, the imaging software is configured to automatically generate customized stereoscopic displays and/or customized projected images, herein called collectively "customized displays." These customized displays are corrected for the refractive aberration of a given user, presenting images that are in focus without requiring the user to wear corrective eyeglasses or corrective lenses in the VR or AR head-mounted display. The customized displays use wavefront aberrometry and scattering maps to model refractive aberrations of a given user.

In an embodiment, the imaging software is configured, for both normal-vision and defective-vision users, to correct undesirable effects such as distortion and chromatic aberration, introduced into images by lenses or other optical elements of the optical path. In an embodiment, the imaging software is configured to provide consistency of focus under different conditions of use of the head-mounted display, such as maintaining focus when a user turns his head.

The head-mounted display 300 of FIG. 3 incorporates imaging software that modifies an expected image to be received by the retina of normal-vision users to take into account refractive corrections for a user with a refractive aberration. Refraction headset 320 automatically collects Refractive Aberration Measurements 330. These objective refraction data are used to calculate Refractive Corrections 340. In an embodiment, the Refractive Corrections 340 automate the principles of Scheiner's disk in computing refractive data in terms of spherical and cylindrical powers. The imaging software generates Corrected Image Data 360 by modifying the Uncorrected Image Data 350 based upon the Refractive Corrections 340, thereby determining stereoscopic images displayed by micro-displays 304, 306 of display screen 302.

In an embodiment, display screen 302 incorporates optically anisotropic hardware, i.e., a programmable light field display. In contrast to conventional displays, which are intended to emit light isotropically, light field displays can modulate radiance as a function of position and direction across their surface. In an illustrative embodiment, the light field display 302 is a two-layered stereoscopic display including a microlens array that separates each image into individual light rays, developed by NVIDIA Corporation, Santa Clara, Calif. (United States Patent Application 20140168783 A1).

In an embodiment, the customized displays pre-warp the light field to counteract the refractive condition of the user's eyes. Pre-warping includes two primary steps: first, pairing light field rays and retinal positions, while associating an intensity value to each ray; and second, normalizing retinal "pixels." The method processes an expected image 350 to be received by the retina of normal-vision users, and a wavefront map of the user's eyes, to produce a light field for a customized display of the head-mounted display. In an embodiment, the wavefront map that controls production of customized stereoscopic displays is an aberration map 330 generated by a wavefront aberrometer of the automated refraction headset 320.

In an embodiment, the customized displays enhance visual acuity by decomposing virtual objects and placing the resulting image components into the user's focal range. The customization process splits an object's light field into multiple instances, each of which is in-focus for a given sub-aperture of the eye. The imaging software uses multiple depths to render each point of focus on the retina, creating multi-focus, multi-depth displays. A customized display method projects depth-dependent patterns based upon the spatially-distributed refractive aberrations of the user's eye. The depth-dependent patterns are anisotropic images, each of which is virtually positioned at the correct point in focus for a given optical power in a section of the user's cornea. The imaging software places these anisotropic images at multiple depths to create a single image in focus. Depth-dependent patches are viewed only through eye sub-apertures with given refractive powers.

The final result is a light field that is customized to be displayed at a given perceived distance from the given user's eyes in the near-to-eye VR or AR head-mounted display. The imaging software integrates these anisotropic images on the retina, thereby resulting in stereoscopic images of enhanced clarity and sharpness in projection for a user with refractive aberration.

In various embodiments, the automated refraction headset stores image-modification software that can be exported to a VR head-mounted display or AR head-mounted display and used by an imaging system of the head-mounted display to modify images to correct for a refractive condition identified by the refraction headset. This feature can be included in a stand-alone refraction headset such as the refraction headset 100 of FIG. 1, and also can be included in a refraction headset designed to serve as a temporary or permanent subassembly of a VR or AR head-mounted display such as the refraction headset 320 of FIG. 3. In an embodiment, the refraction headset stores a library of image-modification software modules respectively designed for specifications of different VR and/or AR head-mounted displays, and/or for different types of display hardware such programmable light field displays. In an embodiment, the refraction headset communicates refractive error measurements to a mobile computing device that controls imaging by an associated head-mounted VR or AR display, and the mobile computing device stores an image-modification software application for auto-calibration of the given VR or AR display. In an embodiment, the mobile computing device stores a library of image-modification software modules respectively designed for specifications of different associated VR and/or AR head-mounted displays.

The foregoing method descriptions and the interface configuration are provided merely as illustrative examples and are not intended to require or imply that the steps of the various embodiments must be performed in the order presented. As will be appreciated by one of skill in the art, the steps in the foregoing embodiments may be performed in any order. Words such as "then," "next," etc., are not intended to limit the order of the steps; these words are simply used to guide the reader through the description of the methods. Although process flow diagrams may describe the operations as a sequential process, many of the operations can be performed in parallel or concurrently. In addition, the order of the operations may be rearranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:

1. A method, comprising:
projecting a grid onto an eye of a user using a light source of a head-mounted display worn by the user;
capturing the grid as-reflected from the eye using a camera of the head-mounted display;
determining a pattern of a reflection of the grid based on the grid as-reflected;
generating an aberration map based on a difference between the pattern as-reflected and the grid as-projected; and
determining a correction to apply to at least one image displayed to the user using at least one viewing lens of the head-mounted display worn by the user based on the aberration map.

2. The method of claim 1, wherein the head-mounted display includes an occluded binocular autorefraction device.

3. The method of claim 1, wherein generating the aberration map is performed using a wavefront aberrometer.

4. The method of claim 1, comprising:
determining another correction to apply to at least another viewing lens of the display worn by the user based on the aberration map.

5. The method of claim 1, wherein the head-mounted display includes a temporary or permanent subassembly of a virtual reality (VR) or an augmented reality (AR) headset.

6. The method of claim 1, wherein the head-mounted display includes a variable focus mirror assembly.

7. The method of claim 1, comprising:
determining objective refraction data, wherein the objective refraction data are spherical error information representative of the aberration comprising one of myopia, hyperopia, and presbyopia, and wherein the determining is based on the objective refraction data.

8. The method of claim 1, comprising:
determining objective refraction data, wherein the objective refraction data are cylindrical error information representative of the aberration including astigmatism, and wherein the determining is based on the objective refraction data.

9. A system comprising:
a head-mounted display configured to display images corresponding to virtual reality or augmented reality;
a light source of the head-mounted display configured to project a grid onto an eye of a user;
a camera of the head-mounted display configured to capture the grid as-reflected from the eye of the user;
a server communicatively coupled to the head-mounted display and configured to:
determine a pattern of a reflection of the grid based on the grid as-reflected;
generate an aberration map based on a difference between the pattern as-reflected and the grid as-projected; and
determine a correction to apply to at least one image displayed to the user using at least one viewing lens of the head-mounted display worn by the user based on the aberration map.

10. The system of claim 9, wherein the head-mounted display includes a stereoscopic display device.

11. The system of claim 10, wherein the stereoscopic display device is a stereoscopic display screen of a virtual reality near-to-eye head-mounted display.

12. The system of claim 10, wherein the stereoscopic display device is an optical projector of an augmented reality near-to-eye head-mounted display.

13. The system of claim 10, wherein the stereoscopic display device is a programmable light field display.

14. The system of claim 9, wherein the display includes an optical projector of an augmented reality near-to-eye head-mounted display.

15. The system of claim 9, wherein the display includes an optical see-through display wherein the user views a physical environment through viewing lenses and the image light is projected by an optical projector through adaptive optics onto viewing lenses, further comprising adaptive secondary lenses that operate in conjunction with the viewing lenses to compensate for the aberration of the at least one of the eyes of the user in the user's view of the physical environment through the viewing lenses.

16. The system of claim 9, wherein the server is configured to determine objective refraction data, wherein the objective refraction data are spherical error information representative of the aberration comprising one of myopia, hyperopia, and presbyopia, and wherein the control is based on the objective refraction data.

17. The system of claim 9, wherein the server is configured to determine objective refraction data, wherein the objective refraction data are cylindrical error information representative of the aberration including astigmatism, and wherein the control is based on the objective refraction data.

18. A computer program product comprising a non-transitory computer-readable medium storing instructions that when used effectuate:

projecting a grid onto an eye of a user using a light source of a head-mounted display worn by the user;

capturing the grid as-reflected from the eye using a camera of the head-mounted display;

determining a pattern of a reflection of the grid based on the grid as-reflected;

generating an aberration map based on a difference between the pattern as-reflected and the grid as-projected; and determining a correction to apply to at least one image displayed to the user using at least one viewing lens of the head-mounted display worn by the user based on the aberration map.

19. The computer program product of claim 18, wherein the head-mounted display includes a variable focus lens assembly.

20. The computer program product of claim 18, wherein the head-mounted display includes an autorefractor or a wavefront aberrometer.

\* \* \* \* \*